United States Patent [19]
Dechow

[11] Patent Number: 4,883,068
[45] Date of Patent: Nov. 28, 1989

[54] BLOOD SAMPLING DEVICE AND METHOD

[75] Inventor: Frederick L. Dechow, Lake Leelanau, Mich.

[73] Assignee: Dec in Tech, Inc., Gillette, N.J.

[21] Appl. No.: 167,778

[22] Filed: Mar. 14, 1988

[51] Int. Cl.$^4$ .............................................. A61B 5/00
[52] U.S. Cl. ................................. 128/760; 128/770; 128/764; 604/413; 604/117; 604/198
[58] Field of Search ............... 128/760, 763, 764, 770; 604/413, 415, 171, 198, 148, 117, 192, 194, 197

[56] References Cited

U.S. PATENT DOCUMENTS

| | | | |
|---|---|---|---|
| 4,295,476 | 10/1981 | Quaas | 128/764 |
| 4,643,199 | 2/1987 | Jennings et al. | 128/763 |
| 4,747,829 | 5/1988 | Jacob et al. | 604/198 X |
| 4,774,964 | 10/1988 | Bonaldo | 128/763 |
| 4,804,371 | 2/1989 | Vaillancourt | 604/198 |
| 4,941,531 | 6/1960 | Stevens | 128/764 |

FOREIGN PATENT DOCUMENTS 1022417 12/1977 Canada ............................ 128/764

Primary Examiner—Max Hindenburg
Assistant Examiner—J. P. Lacyk
Attorney, Agent, or Firm—Learman & McCulloch

[57] ABSTRACT

A disposable blood sampling device wherein inner and outer spaced apart pad members, separated by a compressible pad-bridging enclosure respectively carry an axially extending evacuated collecting container closed by a penetrable end cap and an axially aligned, double-ended cannula. In normal position the cannula is maintained in withdrawn position within the enclosure. The cannula is prevented from penetrating the cap of the collecting tube when the outer member is depressed toward the inner member until after penetration of the epidermis has occurred.

14 Claims, 1 Drawing Sheet

BLOOD SAMPLING DEVICE AND METHOD

This application is directed to disposable blood collection devices and more particularly to a system designed for self use at home.

BACKGROUND OF THE INVENTION

A number of diagnostic procedures can now be performed by the patients at home utilizing relatively small quantities of blood which can be conveniently obtained from capillary blood sources such as a fingertip. While various blood sampling devices have been proposed and are in use, most of them, as exemplified by the following listed patents, are of the type which draw venous blood from patients in a procedure which should be performed by a trained medical technologist:

| | | | |
|---|---|---|---|
| 3,200,813 | Christakis | 4,256,120 | Finley |
| 3,536,061 | Ogle | 4,298,011 | Mangurten et al |
| 3,545,427 | Ryan | 4,409,990 | Mileikowsky |
| 4,024,857 | Blecher et al | 4,418,703 | Hoch et al |
| 4,155,350 | Percarpio | 4,449,529 | Burns et al |
| 4,215,700 | Crouther et al | | |

While not all of the foregoing patents are directed to devices which accumulate venous blood, none have been sufficiently versatile to accomplish all of the objects of the present invention.

SUMMARY OF THE INVENTION

It is an object of the present invention to provide a micro-blood collection device which accumulates the blood flow from a skin or epidermal puncture in a sterile sampler container in a manner which insures that the skin puncture will occur before the double-ended cannula penetrates a cap sealing an evacuated collection chamber.

Still another object of the invention is to provide a blood sampling device of the character described in which the depth of penetration of the double-ended cannula into the tip of the finger, or other selected part of the body, is reliably controlled.

A further object of the invention is to provide a blood sampling device having a box-like housing which hides the double-ended needle from view, and thus reduces the trauma involved in this self-testing procedure.

Still another object of the invention is to provide a blood collection device which is economically manufactured so that it can be used at home with a diagnostic kit, and then thrown away.

Still a further object of the invention is to provide a device which reliably collects the desired volume of blood in a sterile chamber in a very simple manner.

These and other objects of the invention are accomplished in a housing comprising inner and outer spaced apart pads or walls separated by a compressible, axially extending, pad-bridging enclosure. A double-ended cannula is axially slideably carried by the inner pad and is axially aligned with an evacuated collecting tube closed by a penetrable cap. The system is designed to prevent the double-ended cannula from penetrating the cap of the evacuated collecting tube upon compression of the inner and outer pads of the housing, until after penetration of the epidermis by the cannula.

Other objects and advantages of the invention will be pointed out specifically or will become apparent from the following description when it is considered in conjunction with the appended claims and the accompanying drawings.

DESCRIPTION OF THE PREFERRED EMBODIMENTS

Figure 1:
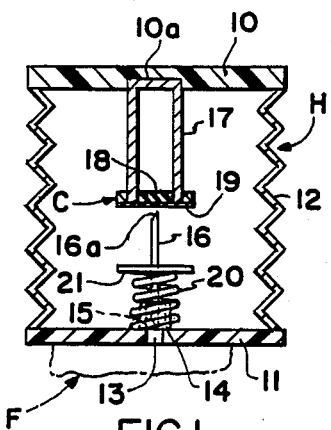
FIG. 1 is a sectional side elevational view showing the device in initial position placed in contact with a tip of a finger or the like which is illustrated in chain lines.
Figure 2:
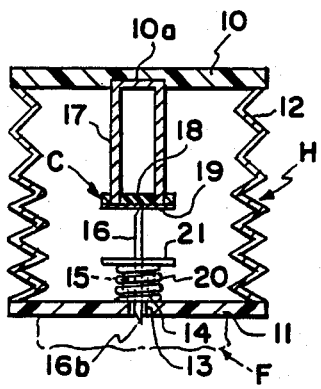
FIG. 2 is a similar view illustrating the position of the component parts when a compression of the housing has occurred and the lower end of the needle or cannula has penetrated the skin of the finger.
Figure 3:
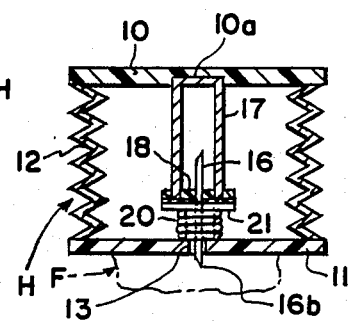
FIG. 3 is a further view illustrating the final position of the various components when a full compression of the device has occurred and blood is being drawn into the sample-collecting tube.

Referring now more particularly to the accompanying drawings, and in the first instance to FIGS. 1–3, rectangular or circular upper and lower pads 10 and 11 are shown connected by an enclosing bellows 12 to form a housing generally designated H. The pads or end wall members 10 and 11 are mentioned as upper and lower members only for the sake of convenience since it should be clear that the device will also be operative when turned on its side. The lower pad 11 is provided with a central bore or opening 13 which can be placed adjacent the tip of a finger generally designated F, for instance, when it is desired to draw a blood sample.

Fixed to the lower member 11 is a rigid tubular guide 14 having an inner passage 15 which accommodates and slidably guides a double-ended cannula or needle 16 having sharpened puncturing ends 16a and 16b. Mounted above the needle is a collection container 17, which is fixed in a well 10a provided in the top member 10. The outer end of chamber 17 is removably closed by a cap assembly, generally designated C, which includes a puncture sealing rubber stopper member 18 inboard of an outer foil cap backer 19. Cap C snugly closes the open end of the tube 17, which is evacuated at the time cap C is tightly applied.

Provided in surrounding relation with the tubular post 14, is a coil spring 20 which exerts a predetermined upward pressure on a stop disk 21 which is fixed to the cannula 16 at a predetermined spaced distance from the lower end of the cannula. The spring 20 normally maintains the cannula 16 in the FIG. 1 position with the lower end 16b of the cannula in axial alignment with the opening 13. The resistance to compression of cannula return spring 20 is such that the lower end of cannula 16 will penetrate the epidermis or skin of the finger F prior to the time the upper end 16a of the cannula 16 penetrates the stopper portion 18. The durometer of stopper 18 is therefore such that its resistance to penetration is greater than the force required to compress spring 20. Thus, both the spring 20 and stopper 18 are carefully engineered so that, when the parts are in the FIG. 2 position, penetration of the skin has occurred prior to the time stopper 18 has been penetrated. With this construction, there is assurance that the vacuum in tube 17 will not be dissipated and will be effective to draw the blood up into the container. The foil 19 is so thin as to offer no appreciable resistance to penetration.

THE OPERATION

In operation, with the device placed in contact with the tip of the finger F as shown in FIG. 1, the pad 10 is depressed toward the lower pad 11 to compress the housing H. As FIG. 2 indicates, the relative resistance to puncture of the rubber 18 and the skin of finger F, taken with the resistance to compression of spring 20, are such that the cannula 16 first penetrates the skin as indicated in FIG. 2. A further compression of the pad 10 toward the pad 11 is illustrated in FIG. 3 and shows the final position of the parts when a blood sample is being delivered to the interior of container 17.

AN ALTERNATIVE PENETRATION CONTROL DEVICE

Figure 4:
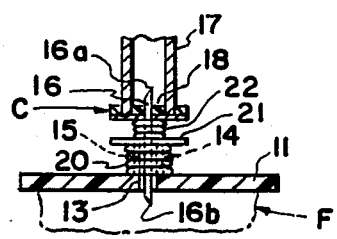
FIG. 4 is a fragmentary view showing the components in the FIG. 3 position and illustrating an alternative construction.

In FIG. 4, a dual-spring device is utilized in which a second stiffer compressible spring 22 surrounds the upper end of the cannula and bears against the upper side of stop 21. Except for this, all of the parts are identical to the components previously described and for purposes of convenience have been identified by the same numerals and will not be redescribed. In this embodiment of the invention, spring 22 acts to increase the resistance to puncture of the cap C, the springs 22 and 16 acting in opposition to one another on opposite sides of the stop 21 to ensure that it is the epidermis of the skin which is punctured prior to puncture of the cap assembly C.

ANOTHER EMBODIMENT OF THE INVENTION

Figure 5:
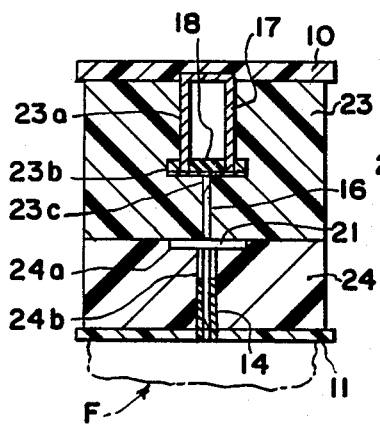
FIG. 5 is a view similar to FIG. 1 wherein another embodiment of the invention is disclosed, wth the components in initial position prior to compression.
Figure 6:
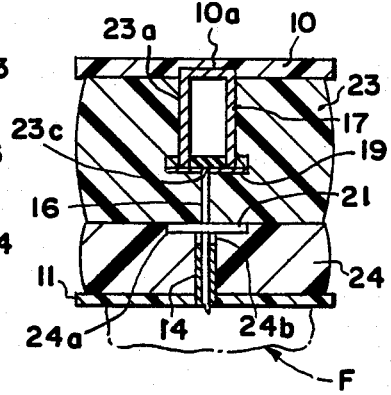
FIG. 6 is a view similar to FIG. 2 in which a partial relative compression of the upper and lower portions of the housing has occurred.
Figure 7:
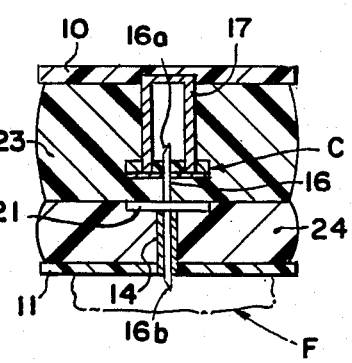
FIG. 7 is a view similar to FIG. 3 in which a full compression of the housing parts has occurred and blood is being drawn up into the sampling chamber.

FIGS. 5-7 illustrate another embodiment of the invention, and in these Figures those components which remain the same have been identified by the same numbers as previously, and the description of these components will not be repeated In this embodiment of the invention, a pair of compressible rigid plastic foams 23 and 24 forming an enclosure for the tube 17 and needle 16 are provided between the pads 10 and 11, and the spring 20 can be eliminated. The upper foam member 23 is recessed as at 23a, 23b, and 23c centrally to receive the container 17 and to provide a passage for cannula 16. The foam layer 24 is recessed as at 24a and 24b to receive the tubular post 14 and the needle stop 21. Foam layer 23 is a more riqid foam than foam 24 and is considerably more resistant to crush than lower foam layer 24.

In operation, when the upper pad 10 is moved toward the lower pad 11 to compress the device the greater resistance to crush of layer 23 ensures penetration of the cannula 16 into the skin to the extent shown in FIG. 6 prior to complete penetration of the cap assembly C. With further compression of the layers 23 and 24 to the FIG. 7 position, blood is being drawn by the vacuum in container 17 up into the container 17 in the same manner as previously. The relative crushability of foam layers 23 and 24, taken with the resistance to puncture of the cap assembly C insures the sequential penetration of the two ends of cannula 16.

It is to be understood that the embodiments described are exemplary of various forms of the invention only and that the invention is defined in the appended claims which contemplate various modifications within the spirit and scope of the invention.

I claim:

1. In a disposable blood sampling device particularly for removing a small volume of blood from the epidermis of the body for testing purposes:
   a. a housing comprising inner and outer, spaced apart, walls separated by an axially compressible, axially extending bridging enclosure;
   b. said outer wall carrying an axially extending, evacuated, collecting container housed within said axially compressible enclosure and having an open end closed by a penetrable end member;
   c. a double-ended cannula device axially slidably carried by said inner wall in axial alignment with said end member, and having an end member-penetrating end and a skin-penetrating end;
   d. said inner wall having a cannula device passing portion in axial alignment with said cannula device for passing the skin-penetrating end through the inner wall into the epidermis; and
   e. means for preventing said cannula device from penetrating the end member of the collecting container when the inner and outer walls are relatively axially compressed, until after penetration of the epidermis by the cannula device.

2. The invention defined in claim 1 in which a dual function tubular guide is provided on said inner wall to project axially toward said outer wall for slidably accommodating said cannula device, and stop means is provided on said cannula device, for interaction with said guide to limit the protrusion of said cannula device from said inner wall.

3. The invention defined in claim 1 in which a means is provided to normally hold the skin penetrating end of he cannula device in retracted position within the inner wall and to limit the permissible protrusion of said cannula device through said inner wall.

4. The invention defined in claim 2 in which a coil spring is provided in engagement with said stop means and inner wall, which functions to normally hold the cannula device in retracted position inboard of the inner surface of the inner wall.

5. The invention defined in claim 1 wherein stop means is provided on said cannula device and said enclosure comprises upper and lower layers of crushable rigid foam in engagement with opposite sides of said stop means adjacent said outer and inner walls respectively, the upper layer adjacent said outer wall having a predetermined greater resistance to axial crush than the lower layer adjacent said inner wall.

6. The invention defined in claim 4 wherein said end member includes a rubber plug; the plug being of a predetermined durometer guaged to offer greater resistance to axial penetration than the resistance required to overcome said spring.

7. The invention defined in claim 4 wherein a second stiffer coil spring is provided on said cannula device on the opposite side of said stop means from the first mentioned spring.

8. The invention defined in claim 1 in which said enclosure comprises an opaque, surrounding member.

9. The invention of claim 8 in which said enclosure is a bellows.

10. The invention defined in claim 1 wherein said outer wall is fixed to one end of said enclosure and to said container.

11. The invention defined in claim 10 wherein said inner wall is fixed to the opposite end of said enclosure.

12. A method of operating a disposable blood sampling device having inner and outer spaced apart wall surfaces separated by an axially compressible, axially extending wall surface-bridging enclosure to form a housing; the outer wall surface carrying an axially extending evacuating collecting tube closed by a penetrable tube end member; a double-ended cannula device axially slidably carried by the inner wall surface in axial alignment with the end member and having an end member-penetrating end and a skin-penetrating end; the inner wall surface having a portion in axial alignment with the cannula device for passing the skin-penetrating end through the inner wall surface into the epidermis; and means for causing the cannula device to penetrate the epidermis prior to penetrating the end member of the collecting tube when the inner and outer wall surfaces are relatively axially compressed comprising the steps of:

a. axially moving the outer wall surface toward the inner wall surface to a predetermined extent to cause the collecting tube to force the skin penetrating end of the cannula device to pass through the inner wall surface and penetrate the epidermis;

b. then engaging the cannula device to halt the movement of the cannula device into the epidermis despite further movement of the outer wall surface toward the inner wall surface and continuing the movement of the outer wall surface toward the inner wall surface to puncture the collecting tube end member; and c. withdrawing the blood into the evacuated collecting tube via the suction forces in the tube.

13. The method defined in claim 12 wherein members provided on the cannula device and on the inner wall surface are engaged to halt the penetration of the cannula device into the epidermis.

14. The method defined in claim 12 wherein said enclosure is formed by a layer of crushable rigid plastic foam enclosing the tube and a second layer of crushable rigid plastic foam enclosing the cannula device; the layer of foam surrounding the sample-collecting tube being more resistant to compressive crush than the second layer of plastic foam so that the layer of foam surrounding the tube is less compressed than the other layer of foam when the outer wall surface is moved toward the inner wall surface and the greater compressibility of the said other layer permits penetration of the epidermis before the compressibility of the layer of foam surrounding the tube permits penetration of the tube end member.

* * * * *